US006980683B2

(12) United States Patent
Jones

(10) Patent No.: US 6,980,683 B2
(45) Date of Patent: Dec. 27, 2005

(54) ON-LINE CORRECTION OF PATIENT MOTION IN THREE-DIMENSIONAL POSITRON EMISSION TOMOGRAPHY

(75) Inventor: William F. Jones, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 591 days.

(21) Appl. No.: 10/179,060

(22) Filed: Jun. 25, 2002

(65) Prior Publication Data

US 2002/0163994 A1 Nov. 7, 2002

Related U.S. Application Data

(63) Continuation-in-part of application No. 09/649,499, filed on Aug. 28, 2000.

(51) Int. Cl.⁷ .............................................. G06K 9/00
(52) U.S. Cl. ................................. 382/131; 250/363.03
(58) Field of Search ................................ 382/103, 128, 382/131, 132, 276, 293; 378/4, 21; 250/363.04, 250/363.03

(56) References Cited

U.S. PATENT DOCUMENTS

| 4,980,552 A | * | 12/1990 | Cho et al. ............... 250/363.03 |
| 5,224,037 A | * | 6/1993 | Jones et al. .................. 382/131 |
| 6,915,004 B2 | * | 7/2005 | Newport et al. ............ 382/131 |

OTHER PUBLICATIONS

B.J. Lopresti et al., "Implementation and Performance of an Optical Motion Tracking System for High Resolution Brain PET Imaging," IEEE Trans. Nucl. Sci., vol. 46, No. 6, 2059-2067 (Dec. 1999).
M. Spiegel, Schaum's Mathematical Handbook, McGraw Hill, p. 49 (1968).
H.S. Stone, "Pipelining as a Design Principle," Introduction to Computer Architecture, 1975, p. 386, Section 9.3.
R. Fulton et al., "Correction for Head Movements in Positron Emission Tomography Using an Optical Motion Tracking System," IEEE NSS MIC Conference Record, Lyon France, Oct. 2000.
M. Casey et al., "A Component Based Method for Normalization in vol. PET," 3D Conference Proceedings, Aixles-bains, 1995.
W. Jones, "PETLINK Guideline," www.cti-pet/bjones.nsf.
Michael V. Green, et al., "Head Movement in Normal Subjects During Simulated PET Brain Imaging with and without Head Restraint," Journal of Nuclear Med., Sep. 1994, vol. 35, No. 9, pp. 1538-1546.

(Continued)

*Primary Examiner*—Jose L. Couso
*Assistant Examiner*—Tom Y. Lu
(74) *Attorney, Agent, or Firm*—Pitts & Brittian, P.C.

(57) ABSTRACT

A device and method for on-line correction of patient motion in three-dimensional positron emission tomography. The devices encompass an on-line hardware pipelining architecture to support 3D translation, normalization, and weighted histogramming as required. Five stages of processing for the PET event stream are utilized in the present invention. Each stage feeds the next with progressively modified event packets proceeding at a processing speed of at least 10M packets/sec. Stage 1 calculates an event correction factor (ECF) for each incoming detector-pair event packet. This ECF is incorporated into the event packet for use later in Stage 5. Stage 2 converts the detector-index-pair content of each packet into (x,y,z) pair content. Specifically, the representation of each detector element is converted from a discrete crystal index into a 3-D coordinate index. Stage 3 transforms the (x,y,z) pair into an (x',y',z') pair. Stage 4 converts the (x',y',z') pair into a bin address. Output from Stage 5 is a normalized projection data set available at the end of each acquisition frame. Stage 5 performs on-line weighted histogramming.

13 Claims, 4 Drawing Sheets

OTHER PUBLICATIONS

Ruttiman, Andreassen, and Rio, Psychiatry Res.: Neuroimaging, 1995, vol. 65: 41-43.

Y. Picard, et al, "Digitized Video Subject Positioning and Surveillance System for PET," IEEE Trans. on Nuclear Science, Aug. 1995, vol. 42, No. 4, pp. 1024-1029.

Y. Picard, et al, "Motion Correction of PET Images Using Multiple Acquisition Frames," IEEE Transactions on Medical Imaging, Apr. 1995, vol. 16, pp. 137-144.

Seth R. Goldstein, et al, "A Head Motion Measurement System Suitable for Emission Computed Tomography," IEEE Trans. on Medical Imaging, Feb. 1997, vol. 16, No. 1, pp. 17-27.

M. Menke, et al, "Compensation Methods for Head Motion Detected During PET Imaging," IEEE Transactions on Nuclear Science, Feb. 1996, vol. 43, Issue 1, pp. 310-317.

* cited by examiner

ON-LINE CORRECTION OF PATIENT MOTION IN THREE-DIMENSIONAL POSITRON EMISSION TOMOGRAPHY

CROSS-REFERENCE TO RELATED APPLICATIONS

This application is a continuation-in-part of Ser. No. 09/649,499, filed on Aug. 28, 2000.

STATEMENT REGARDING FEDERALLY SPONSORED RESEARCH OR DEVELOPMENT

Not Applicable

BACKGROUND OF THE INVENTION

1. Field of Invention

This invention relates to the field of positron emission tomography (PET). More specifically, the present invention is related to a device and method for improving PET resolution through on-line correction of patient motion.

2. Description of the Related Art

In the art of PET detection, it is known that the resolution of a scan is in part dependent upon the amount of motion of the patient during the scan, and specifically the motion of the portion of the body being scanned. It is known that typical PET scans last from fifteen (15) minutes to three (3) hours. Ideally, if the patient could lie motionless during a PET scan, a high resolution PET system such as the CTI Pet Systems, Inc., EXACT HR+ is capable of 4 to 5 mm 3-D image resolution. However, if the patient or object in the field of view (FOV) does not remain stationary, the PET image is blurred. Practically speaking, inadvertent or disease-induced patient motion over the course of the scan currently blurs the 4 to 5 mm resolution to a far less effective 10 to 15 mm or worse.

Recent work has shown that techniques exist for tracking patient motion during the PET scan. B. J. Lopresti et al., "Implementation and Performance of an Optical Motion Tracking System for High Resolution Brain PET Imaging," *IEEE Trans. Nucl. Sci.*, Vol. 46, No. 6, 2059–2067 (Dec. 1999), shows effective tracking of patient head motion to all 6 degrees of 3-D movement. Specifically, they show tracking of the X, Y, and Z offsets to an accuracy of fractions of a millimeter, as well as yaw, pitch, and roll to acceptable angular accuracy. Encouraged by Lopresti's effort, the industry is currently moving toward both partial and more complete analytical solutions to the blurring problem. Partial solutions include gating the PET data into time slices during which the patient is shown to be more stationary. In more complete solutions the measured head position is applied to small time slice groups of PET data or even grouped with individual detector-pair event PET data in list mode form. These solutions each apply a correction for patient motion after the PET scan has completed. The most likely application of the more complete correction is a list mode approach in which all the raw PET data is collected in a computer disk file. After the PET scan completes the data is reprocessed. While this event-by-event list mode approach corrects for the motion of, for example, a patient's head, the reprocessing of the file data is a time consuming task.

In clinical PET applications, economic pressures demand high patient throughput without compromise to ease of use. The aforementioned list mode approach to motion deblurring is problematic in view of these economic pressures in that more operator interaction and unacceptably long processing times are required. Either the data that is stored for reprocessing must be moved to a separate processor, or the data is reprocessed on the computer used for scanning. For a typical scan of 30–45 minute duration, reprocessing the data requires 30 minutes to 3 hours of scanner time (equivalent to approximately one to six additional scans) or an independent computing system. Taking this further, if the PET scanner is to be used almost continuously for scanning only, it will be seen that several independent computing systems are required to reprocess the data collected in a most time-efficient manner.

Typically, with respect to PET, the skull and brain are considered a single, rigid object. However, whole body PET scans also suffer from a lack of correction for motion. While problems limit effectiveness compared to brain scans, gross motions of the whole human body may also be de-blurred. PET cardiac gating is one example of a well-known but crude method to compensate for the motion of the heart during a PET scan. Difficult technical challenges remain to more effectively correct for the relative motions between and within individual organs such as, among others, the heart, lungs, liver, and lymph nodes.

Another known obstacle to on-line motion correction in the context of most existing PET applications is on-line normalization. In standard PET, on-line histogramming permits an accumulating tally of true events to be recorded in computer memory bins. One bin is typically reserved for each line of response (LOR) or small group of LORs. Histogramming adds (or subtracts) unity to a designated memory bin for each prompt (or delayed) event. Normalization serves to compensate for variations in detector pair efficiency by scaling the bin values. This scaling is typically applied after histogramming completes and is almost never applied in any on-line or real-time fashion. To apply normalization in real time for typical human PET requires somewhat more complex electronic systems than are in typical use today. These on-line systems must rapidly add or subtract scalar values instead of unity.

Mathematical techniques for transformation from one 3-D coordinate system to another are well known. M. Spiegel, *Schaum's Mathematical Handbook*, McGraw Hill, p. 49 (1968), lists equations for translation and rotation from one 3-D coordinate system (x, y, z) to another (x', y', z'). Representative equations are as follows:

$$x' = d_{xx}*x + d_{xy}*y + d_{xz}*z + X \quad (1)$$

$$y' = d_{yx}*x + d_{yy}*y + d_{yz}*z + Y \quad (2)$$

$$z' = d_{zx}*x + d_{zy}*y + d_{zz}*z + Z \quad (3)$$

where:

X, Y, and Z are translational offsets from the coordinate system (x, y, z) to the coordinate system (x', y', z');

$d_{xx}$, $d_{xy}$, and $d_{xz}$ are direction cosines between the x-, y-, and z-axes and the x' axis, respectively;

$d_{yx}$, $d_{yy}$, and $d_{yz}$ are direction cosines between the x-, y-, and z-axes and the y' axis, respectively; and $d_{zx}$, $d_{zy}$, and $d_{zz}$ are direction cosines between the x-, y-, and z-axes and the z' axis, respectively.

These three equations require nine multiplication operations and three operations involving the addition of four input variables.

The known digital electronic technique of pipelining is applied to arithmetic operations such that the speed of the electrical circuit is limited not by the whole computation but instead by the slowest individual piece of the computation. See Introduction to Computer Architecture by H. S. Stone, 1975, page 386, Section 9.3, "Pipelining as a Design Principle". However, such technique has not been shown in the prior art to be successful in the environment of on-line correction of patient data in a PET scan to account for patient motion.

BRIEF SUMMARY OF THE INVENTION

The present invention serves to apply a correction for patient motion in an on-line and real-time manner. The present invention further provides a means whereby as each PET coincidence event is detected, each line of response (LOR) is re-mapped or rebinned in real time from a stationary 3-D reference space of the PET detector array into a virtual 3-D reference space which moves dynamically with the patient. On-line normalization is also applicable to properly histogram events which are corrected for patient movement.

Five stages of processing for the PET event stream are utilized in the present invention. Each stage feeds the next with progressively modified event packets proceeding at a processing speed of at least 10M packets/sec. Stage 1 calculates an event correction factor (ECF) for each incoming detector-pair event packet. This ECF is incorporated into the event packet for use later in Stage 5. Stage 2 converts the detector-index-pair content of each packet into (x,y,z) pair content. Specifically, the representation of each detector element is converted from a discrete crystal index into a 3-D coordinate index. Stage 2 is a cascade of flash memory look-up tables. Stage 3 transforms the (x,y,z) pair into an (x',y',z') pair. Stage 4 is another cascade of flash memory having some arithmetic processing. Stage 4 converts the (x',y',z') pair into a bin address. Stage 5 contains one or more DRAM banks with some local arithmetic processing. Output from Stage 5 is a normalized projection data set available at the end of each acquisition frame. Pipelining is used as needed throughout the architecture to preserve throughput. Sustainable event throughput is at least 10M packets/sec. Stage 5 performs on-line weighted histogramming.

In Stage 3, the present invention incorporates a core hardware pipelining architecture to perform the transformation between 3-D coordinate spaces as required. A first digital pipeline latch is provided for receiving coincidence event and patient position data when collected by the PET scanner. A bank of multiplier circuits receives the PET scan data. Each multiplier circuit receives and multiplies a respective portion of each data set simultaneous with each of the other multiplier circuits. The product of each multiplier circuit is output to a second digital pipeline latch. The data is then passed to a bank of adders, each of which supports four input variables.

While data for a specific LOR and a current object orientation are input to the first digital pipeline latch, processing for a different LOR and an earlier object orientation (limited to the 3 translation offsets, X Y Z) are stored in the second digital pipeline latch. Additionally, fully transformed coordinates from a third LOR are loaded into a third digital pipeline latch. As the banks may each complete their respective tasks under a threshold time limit, the pipelining technique permits the entire 3-D transformation for the "AB" gamma coincidence detector pair to take place in real time.

In event-by-event normalization (Stage 5), a scalar value typically in the range of 0.01 to 100 is added to (or subtracted from) the indicated projection space bin value for each LOR prompt (or delayed). For on-line correction of object motion, the normalization is applied in an on-line fashion. The result of on-line normalization is that the final total projection bin values are scaled to properly correct for variations in detector efficiency and dead time.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A device and method for on-line correction of patient motion in three-dimensional positron emission tomography (3D PET) incorporating various features of the present invention is illustrated generally at 10 in the figures. The device for on-line correction of patient motion in 3D PET, or device 10, is designed to apply a correction for patient motion in an on-line and real-time manner. Moreover, the device 10 provides a means whereby as each PET coincidence event is detected, each line of response (LOR) is re-mapped or rebinned in real time from a stationary 3-D reference space of the PET detector array into a virtual 3-D reference space which moves dynamically with the patient.

As discussed previously, with respect to PET, the skull and brain are typically considered a single, rigid object. Accordingly, correction for subtle patient head motion is effective for typical PET operation. However, whole body PET scans also suffer from a lack of correction for motion. Accordingly, it is within the scope of the present invention to track and correct for the gross motions of the human—treated as a single rigid object or as a collection of rigid objects. For example, it is foreseeable by one skilled in the art that the present invention, if replicated within each PET device, be used to differentially track the upper chest and hips as two separate rigid bodies. Similarly, the present invention may be used to simultaneously track the head, upper chest, hips, upper arm, lower leg, etc.

Figure 1:
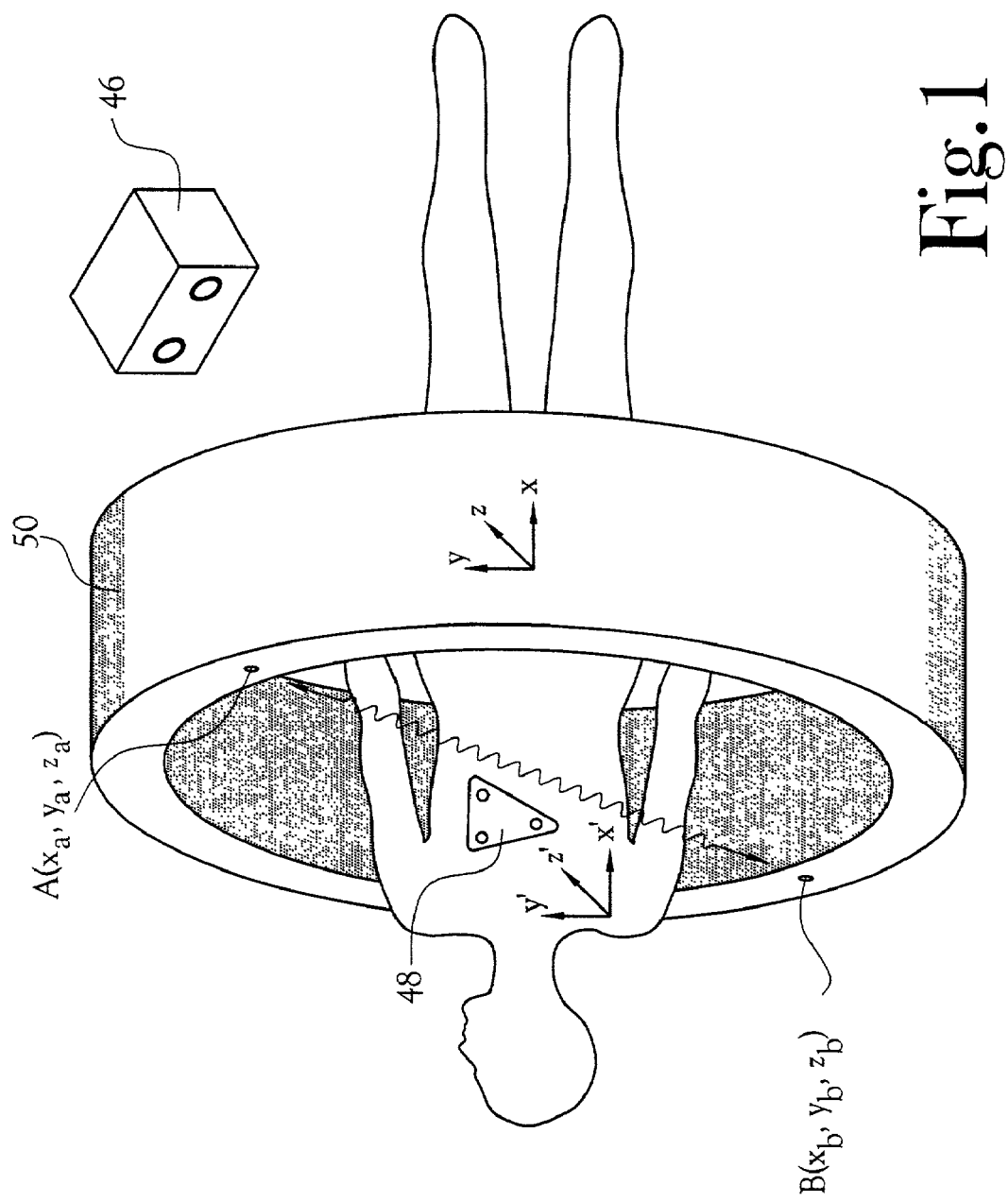
FIG. 1 illustrates a patient received within the FOV of a PET detector array, wherein a reference marker is attached to the patient's chest and a motion tracking device is provided for tracking the reference marker in real time for six degrees of movement.

FIG. 1 illustrates a patient received within the FOV of a PET detector array 50. A reference marker 48 is attached to the patient's chest. A motion tracking device 46 such as a binocular machine vision device, Polaris, manufactured by NDI, (www.ndigital.com/Polaris.html) tracks the reference marker 48 in real time for six degrees of movement. Namely, the motion tracking device 46 tracks movements in the x-, y-, and z-directions, as well as yaw, pitch and roll.

For correction of single rigid body motion in PET, two coordinate spaces are defined. A detector space (x, y, z) represents the coordinates fixed in relation to the 3-D array of PET detectors 50. An object space (x', y', z') represents the virtual 3-D coordinates fixed in relation to an object in the FOV. For any given PET coincidence event, a pair of crystal locations given in x-, y-, z-coordinates represents a detector-pair LOR. The first crystal A of a coincidence pair AB is referenced as residing in the unique detector location $(x_a, y_a, z_a)$. The second crystal B is referenced as residing in detector location $(x_b, y_b, z_b)$.

Figure 2:
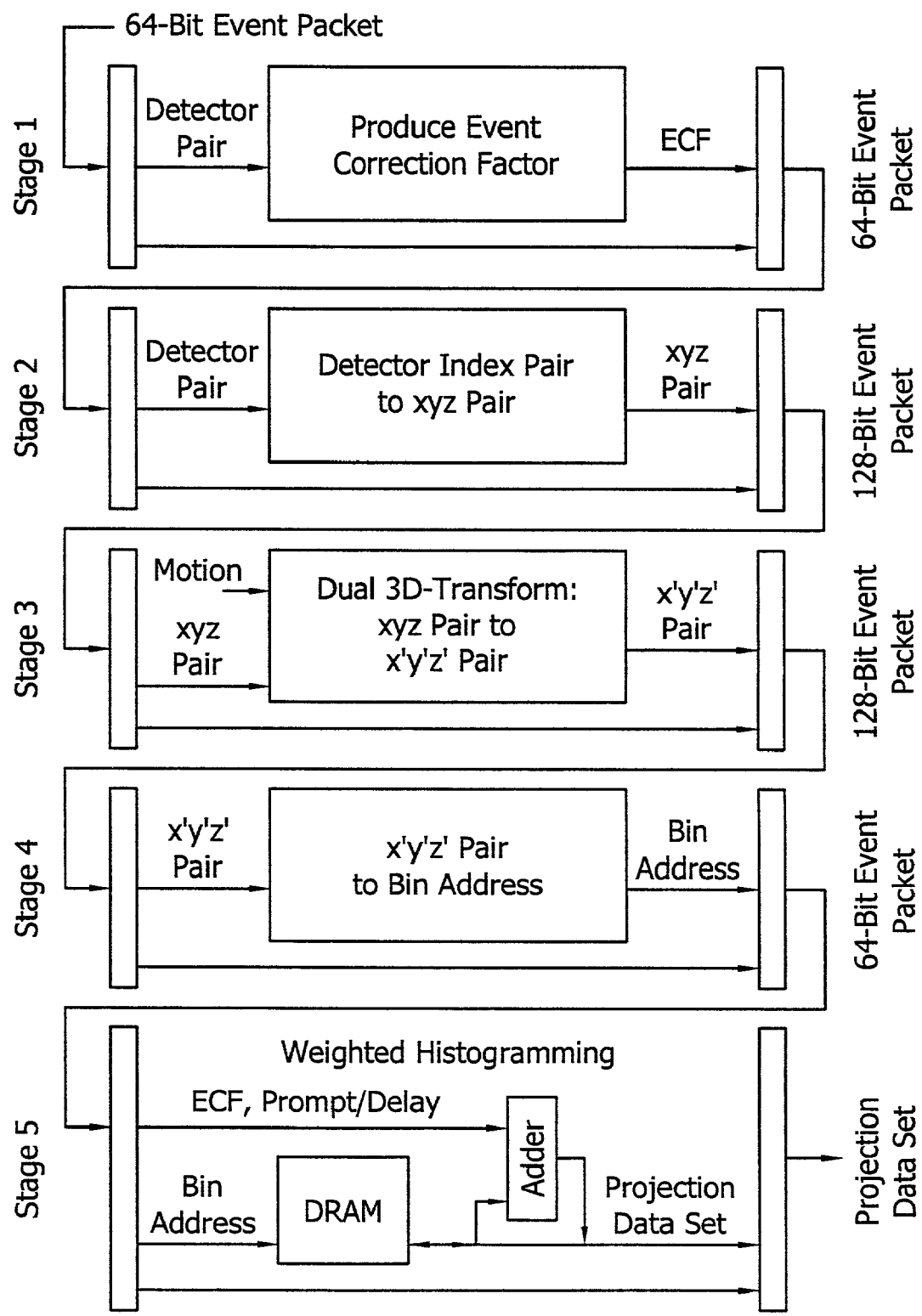
FIG. 2 illustrates a block diagram of the circuitry of the present invention for real-time correction of patient motion.

A block diagram for real-time correction of patient motion is illustrated in FIG. 2. Five stages of processing for the PET event stream are depicted. Each stage feeds the next with progressively modified 64-bit or larger event packets proceeding at a processing speed of at least 10M packets/sec. Stage 1 calculates a 16-bit block-floating event correction factor ECF for each incoming detector-pair event packet. This ECF is incorporated into the 64-bit event packet for use later in Stage 5. For example, the ECF may represent correction for variable detector efficiency, or normalization, and dead time. The operation of Stage 1 is more clearly depicted in FIG. 3 and described in greater detail below.

Stage 2 converts the detector-index-pair content of each packet into (x,y,z) pair content. Specifically, the representation of each detector element is converted from a discrete crystal index into a 3-D coordinate index. Each x, y, and z coordinate is a 12-bit signed integer. Stage 2 is a cascade of flash memory look up tables having a total capacity of at least 128M bytes and at least one simple arithmetic-processing block.

Stage 3 transforms the (x,y,z) pair into an (x',y',z') pair. The operation of Stage 3 is more clearly depicted in FIG. 4 and described in greater detail below.

Stage 4 is another cascade of flash memory having a total capacity of at least 300 Mbytes, also with some arithmetic processing. Stage 4 converts the (x',y',z') pair into a bin address. The 37-bit bin address references a unique element, a 32-bit bin, in the projection data set.

Stage 5 contains one or more DRAM banks with some local arithmetic processing. For example, at least one 32-bit adder may be included. Each DRAM bank has a capacity of at least 128 Mbytes. Output from Stage 5 is a normalized projection data set available at the end of each acquisition frame. Pipelining is used as needed throughout the architecture to preserve throughput. Sustainable event throughput is at least 10M to 12M packets/sec. Stage 5 performs on-line weighted histogramming. In the case of a prompt (or delayed) event, the ECF value is added to (or subtracted from) the content of the indicated bin in the projection data set. At the end of each acquisition frame, the projection data set is available for image reconstruction.

Figure 3:
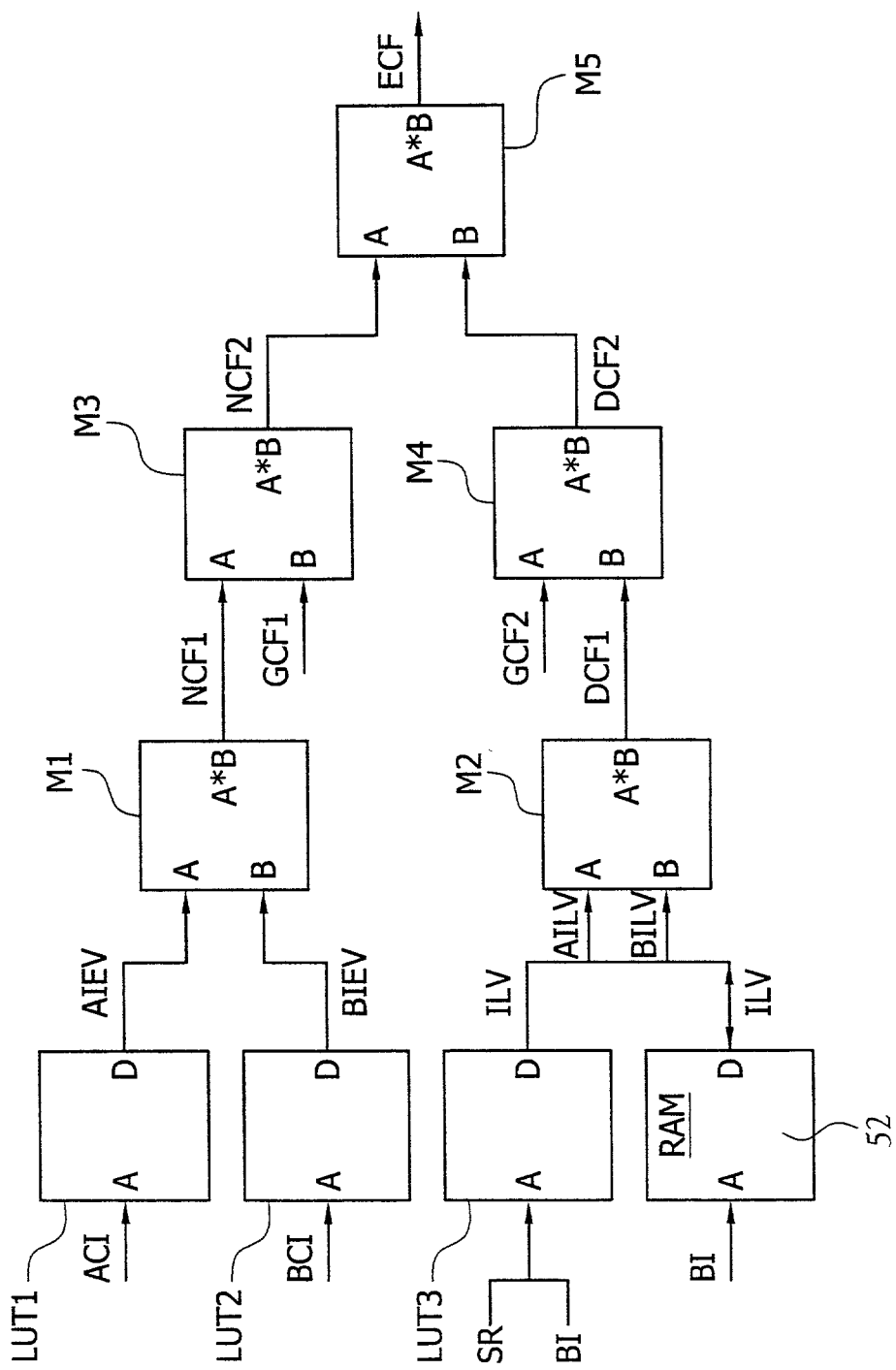
FIG. 3 illustrates a block diagram for on-line generation of coincidence-by-coincidence event correction factors in Stage 1 of the present invention illustrated in FIG. 2.

FIG. 3 illustrates a block diagram for on-line generation of coincidence-by-coincidence ECFs in Stage 1 of FIG. 2. Illustrated is a digital electronic circuit for real-time calculation of normalization and dead-time correction factors. A plurality of look-up table blocks LUT1,LUT2,LUT3 is included, each being a single flash memory chip. A single random-access memory (RAM) chip 52 is also included, as well as a plurality of integer multiplier blocks M1,M2,M3, M4,M5. A calculation of a correction factor for variable detector efficiency, or normalization, is performed with look-up tables LUT1 and LUT2, and integer multipliers M1 and M3. Indexes for 1 of 250,000 individual scintillator crystals (ACI, BCI) are applied as look-up table addresses. Inverse efficiency values AIEV, BIEV are produced from gamma singles rates pre-measured from flooding into the PET scintillator array 50. The integer multiplier M1 multiplies the inverse efficiency values AIEV and BIEV to attain an initial normalization correction factor NCF1. The normalization correction factor NCF1 is then multiplied by a geometric correction factor GCF1 by the integer multiplier M3 to generate a final normalization correction factor NCF2. The geometric correction factor GCF1 is generated by circuitry not illustrated.

Look-up table LUT3 supplies a predetermined conversion of one of a plurality of crystal blocks BI and polled block singles rates SR to provide an inverse "live-time" value ILV. In one embodiment, 512 such crystal blocks are provided. For each arrival of a stream packet for block singles polling, an inverse live-time ILV value is written into the RAM block 52 with a block index BI. For each arrival of a stream packet for a coincidence event, the RAM block 52 is read twice to produce inverse live-time values AILV, BILV. The integer multiplier M2 multiplies the inverse live-time values AILV and BILV to attain an initial dead-time correction factor DCF1. The dead-time correction factor DCF1 is then multiplied by a geometric correction factor GCF2 by the integer multiplier M4 to generate a final dead-time correction factor DCF2. The geometric correction factor GCF2 is generated by circuitry not illustrated.

The integer multiplier M5 multiplies the normalization correction factor NCF2 and the dead-time correction factor DCF2 to produces the event correction factor ECF. This ECF value is inserted into the 64-bit coincidence event packet for use later in Stage 5. Pipelining is used as needed throughout the circuit to preserve throughput. This circuit is capable of operating at over 10M to 12M event stream packets/second.

At the beginning of the scan the object 3-D coordinate space is arbitrarily defined to be the same as that defined for the detector space. Specifically, the nine values X, Y, Z, $d_{xy}$, $d_{xz}$, $d_{yx}$, $d_{yz}$, $d_{zx}$, and $d_{zy}$ from Eqs. 1–3 are all zero and the values $d_{xx}$, $d_{yy}$, and $d_{zz}$ are all unity. As the scan progresses and object motion occurs, the translation offsets and direction cosine values vary. The translation offsets and direction cosines are extracted in real time from the motion tracking device 46. In order to correct for the motion of the object relative to the detector array, object coordinates are calculated for the two crystal locations in real time. The "A" detector location in object space is $(x_a', y_a', z_a')$. The "B" location in object space is $(x_b', y_b', z_b')$. The transformation equations, Eqs. 1–3 listed above, are applied both for the "A" detector position and the "B" detector position. Transformation of the "A" detector location from detector space to object space is as follows:

$$x_a' = d_{xx}*x_a + d_{xy}*y_a + d_{xz}*z_a + X \quad (1a)$$

$$y_a' = d_{yx}*x_a + d_{yy}*y_a + d_{yz}*z_a + Y \quad (2a)$$

$$z_a' = d_{zx}*x_a + d_{zy}*y_a + d_{zz}*z_a + Z \quad (3a)$$

Likewise, transformation of the "B" detector location from detector space to object space is as follows:

$$x_b' = d_{xx}*x_b + d_{xy}*y_b + d_{xz}*z_b + X \quad (1b)$$

$$y_b' = d_{yx}*x_b + d_{yy}*y_b + d_{yz}*z_b + Y \quad (2b)$$

$$z_b' = d_{zx}*x_b + d_{zy}*y_b + d_{zz}*z_b + Z \quad (3b)$$

As current state-of-the-art PET systems detect and generate up to twelve million AB pairs per second (or more), the task is to calculate these 2 transformation equation sets every 83 nanoseconds (or less).

Figure 4:
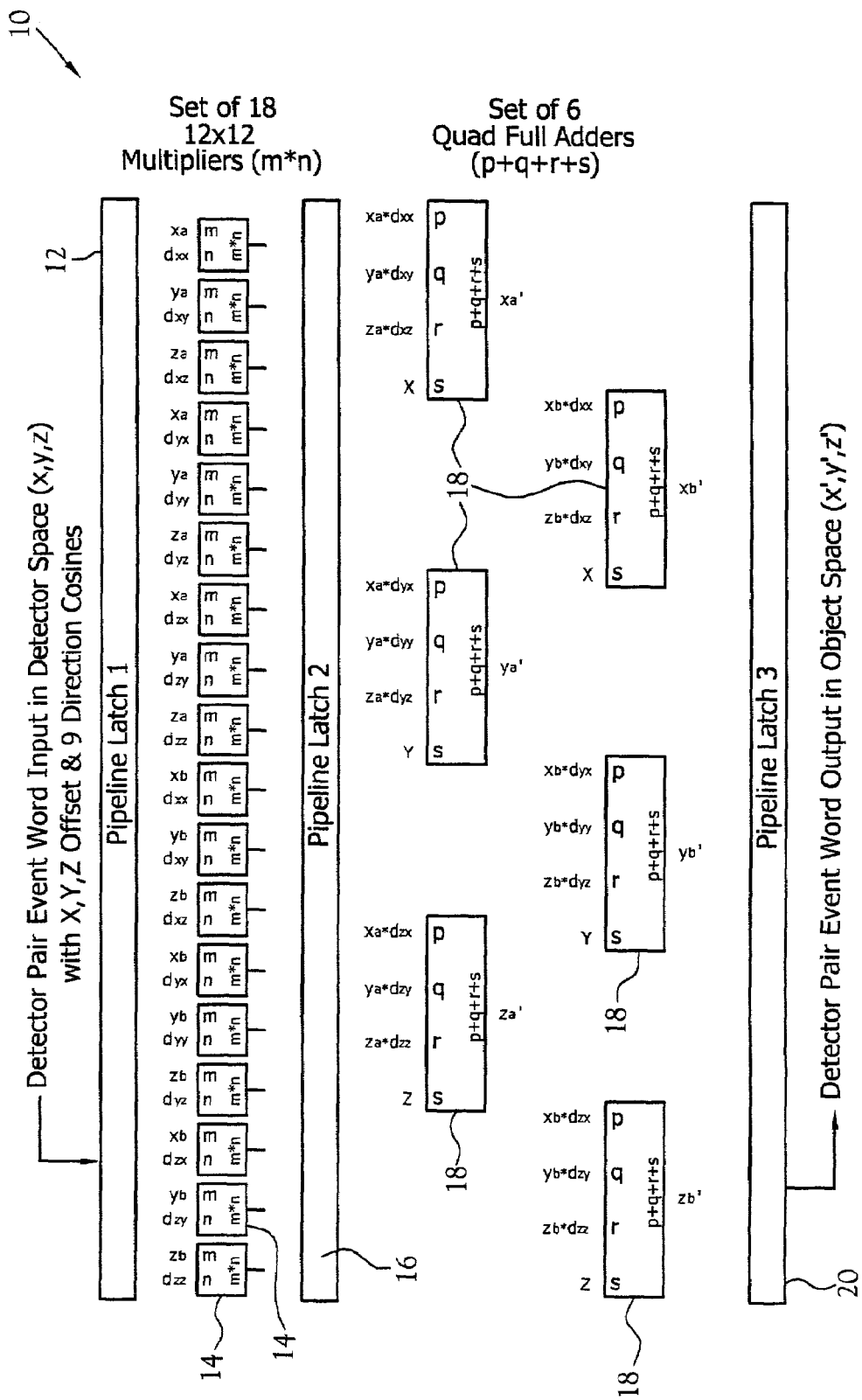
FIG. 4 is a schematic of the core hardware pipelining architecture for performing on-line correction of patient motion in three-dimensional positron emission tomography, as is represented by Stage 3 of FIG. 2.

Illustrated in FIG. 4 is a diagram of the 3-D transformation hardware pipelining architecture 10 of the present invention. A first digital pipeline latch 12 is provided for receiving data as it is collected by the PET scanner. A bank of multiplier circuits 14 receives the PET scan data. Each multiplier circuit 14 receives and multiplies a respective portion of the current LOR and positional data set simultaneously with each of the other multiplier circuits 14. Thus, the multiplier circuits 14 collectively function simultaneously. In the preferred embodiment, each multiplier circuit 14 performs its computation in no more than 83 ns. Illustrated are 18 multiplier circuits 14 for providing 18 integers. The product of each multiplier circuit 14 is output to a second digital pipeline latch 16. Also, the X, Y & Z translational offset variables are passed from the first latch 12 to the second 16. From the second latch 16, the data set is then passed to a bank of adders 18, each of which supports four input variables. Each input variable consists of 12 to 24 bits. Illustrated are six adders 18. The adders 18 also operate simultaneously and in less than 83 ns.

While a specific LOR and a current object orientation are input to the first digital pipeline latch 12, processing for a different LOR and an earlier object X, Y and Z offset are stored in the second digital pipeline latch 16. Additionally and simultaneously, fully transformed ($x_a'$, $y_a'$, $z_a'$, $x_b'$, $y_b'$, $z_b'$) coordinates from a third LOR are loaded into a third digital pipeline latch 20. As the banks shown may each complete their respective tasks in 83 ns or less, the pipelining technique permits the entire 3-D transformation for the AB pair to take place on a sustained basis of twelve million events per second.

In addition to on-line 3-D coordinate transformation, on-line normalization is required for effective motion correction in PET. In typical PET practice, normalization is required and applied after histogramming. For this normalization, a scalar value, typically in the range of 0.001 to 100, is determined and applied to the already histogrammed projection bin data. These scalar values are determined to correct for various points of detector nonuniformity. These points of nonuniformity include variations in detector-to-detector sensitivity, dead-time losses, and the like. In some PET systems, an array of scalar values is produced and maps one-to-one with the array of projection bins. Here each final value in the scalar array is computed as the product of individual normalization correction values. Other PET systems, taking advantage of inherent patterns of uniformity and predictability, may effectively apply normalization correction by processing a much smaller array of normalizing scalar values. For example, PET tomographs which rotate have very uniform sensitivity among the groups of projection bins with equal radial distance from the FOV center. Also, PET tomographs which employ continuous bed motion enjoy very uniform sensitivity from projection bin to projection bin along the FOV axis. This uniformity comes as a result of each and every FOV plane being serviced by each and every tomographic projection bin. In addition, predictable patterns of detector sensitivity exist across the transaxial extent of the FOV. Such patterns of detector sensitivity allow a small list of scalar values to correct for this variation among a very large number of projection bins. In the present invention, the final scalar values may be computed as the product of these various normalization component values.

In typical PET practice, each composite scalar value is simply applied as a multiplication to the respective bin values and only the resulting products of bin values and scalar values are used for further data processing, such as for image reconstruction. In contrast, on-line normalization must be applied as a part of a "weighted" histogramming process. For systems employing weighted histogramming with on-line normalization, histogramming no longer consists of the addition or subtraction of unity to/from respective projection bins. Instead, weighted histogramming with on-line normalization consists of the addition or subtraction of scalar integer values.

From the foregoing description, it will be recognized by those skilled in the art that a device for on-line correction of patient motion in 3D PET offering advantages over the prior art has been provided. Specifically, the device is designed to apply a correction for patient motion in an on-line and real-time manner. The device provides a means whereby as each PET coincidence event is detected, each line of response (LOR) is re-mapped or rebinned in real time from a stationary 3-D reference space of the PET detector array into a virtual 3-D reference space which moves dynamically with the patient. The de-blurring of the PET data is accomplished through the combination of normalization, 3-D translation, and weighted histogramming. As described the system operates at 10M to 12M coincidence events/sec and delivers significantly better PET image resolution for both brain and whole-body studies. Applicable to most commercial PET tomographs, the architecture of the present invention preserves high patient throughput in the clinical setting.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the general inventive concept.

I claim:

1. A device for on-line correction of patient motion in three-dimensional positron emission tomography wherein a positron emission tomograph device is used to collect coincidence event and position data, said device comprising:
   first processing circuitry for calculating an event correction factor (ECF) for said coincidence event and position data;
   second processing circuitry for converting said coincidence event and position data into (x,y,z) pair content;
   third processing circuitry for transforming said (x,y,z) pair into an (x',y',z') pair;
   fourth processing circuitry for converting said (x',y',z') pair into a bin address; and
   fifth processing circuitry for performing on-line weighted histogramming on said bin address using said ECF, said fifth processing circuitry outputting a normalized projection data set.

2. A method for on-line correction of patient motion in three-dimensional positron emission tomography wherein a positron emission tomograph device is used to collect coincidence event data, said method comprising the steps of:
   a) collecting data relative to a scan;
   b) calculating an event correction factor (ECF) for said coincidence event and position data;
   c) converting said coincidence event and position data into (x,y,z) pair content;
   d) transforming said (x,y,z) pair into an (x',y',z') pair;
   e) converting said (x',y',z') pair into a bin address; and
   f) performing on-line weighted histogramming on said bin address using said ECF, outputting a normalized projection data set.

3. A device for on-line correction of patient motion in three-dimensional positron emission tomography wherein a positron emission tomograph device is used to collect coincidence event and position data, said device comprising:

first processing circuitry for calculating an event correction factor (ECF) for said coincidence event and position data, said first processing circuitry including:
a first integer multiplier for multiplying a first inverse efficiency value from a first look-up table and second inverse efficiency value from a second look-up table to attain a first normalization factor, said first inverse efficiency value being representative of a first crystal index, and said second inverse efficiency value being representative of a second crystal index;
a second integer multiplier for multiplying said first normalization factor with a first geometric correction factor to attain a second normalization correction factor;
a third integer multiplier for multiplying an inverse live-time value from a third look-up table and an inverse live-time value from a random access memory (RAM) to attain a first dead-time correction factor, said third look-up table inverse live-time value being a conversion of a crystal block and polled block singles rates, said RAM inverse live-time value being representative of said crystal block;
a fourth integer multiplier for multiplying said first dead-time correction factor with a second geometric correction factor to attain a second dead-time correction factor; and
a fifth integer multiplier for multiplying said second normalization correction factor with said second dead-time correction factor to attain said event correction factor;
second processing circuitry for converting said coincidence event and position data into (x,y,z) pair content;
third processing circuitry for transforming said (x,y,z) pair into an (x',y',z') pair;
fourth processing circuitry for converting said (x',y',z') pair into a bin address; and
fifth processing circuitry for performing on-line weighted histogramming on said bin address using said ECF, said fifth processing circuitry outputting a normalized projection data set.

4. A device for on-line correction of patient motion in three-dimensional positron emission tomography wherein a positron emission tomograph device is used to collect coincidence event and position data, said device comprising:
first processing circuitry for calculating an event correction factor (ECF) for said coincidence event and position data;
second processing circuitry for converting said coincidence event and position data into (x,y,z) pair content;
third processing circuitry for transforming said (x,y,z) pair into an (x',y',z') pair, said third processing circuit including:
a first digital pipeline latch for receiving said data collected by said positron emission tomograph device;
a plurality of multipliers disposed in parallel, each of said plurality of multipliers for receiving and multiplying a portion of said data to generate a product simultaneous with each other of said plurality of multipliers;
a second digital pipeline latch for simultaneously receiving said product from each of said plurality of multipliers;
a plurality of adders disposed in parallel, each of said plurality of adders for receiving and summing a plurality of said product from said plurality of multipliers; and
a third digital pipeline latch for receiving data from said plurality of adders, said data being representative of a pair of transformed coordinate points from a primary coordinate system to a secondary coordinate system;
whereby as said data is input to said first digital pipeline latch, said product of said data from an immediately previous said event is input to said second digital pipeline latch and completely transformed data from a second immediately previous said data is input to said third digital pipeline latch, and whereby said event data is transformed from said primary coordinate system to said secondary coordinate system in real time;
fourth processing circuitry for converting said (x',y',z') pair into a bin address; and
fifth processing circuitry for performing on-line weighted histogramming on said bin address using said ECF, said fifth processing circuitry outputting a normalized projection data set.

5. The device of claim 4 wherein said plurality of multipliers and said plurality of adders are provided to produce transformed coordinates from said primary coordinate system to said secondary coordinate system for each of a pair of detectors using the equations:

$$x_a' = d_{xx}*x_a + d_{xy}*y_a + d_{xz}*z_a + X; \quad (1)$$

$$y_a' = d_{yx}*x_a + d_{yy}*y_a + d_{yz}*z_a + Y; \quad (2)$$

$$z_a' = d_{zx}*x_a + d_{zy}*y_a + d_{zz}*z_a + Z; \quad (3)$$

$$x_b' = d_{xx}*x_b + d_{xy}*y_b + d_{xz}*z_b + X; \quad (4)$$

$$y_b' = d_{yx}*x_b + d_{yy}*y_b + d_{yz}*z_b + Y; \quad (5) \text{ and}$$

$$z_b' = d_{zx}*x_b + d_{zy}*y_b + d_{zz}*z_b + Z; \quad (6)$$

where:
X, Y, and Z are translational offsets from a point (x, y, z) in said primary coordinate system to a point (x', y', z') in said secondary coordinate system;
$d_{xx}$, $d_{xy}$, and $d_{xz}$ are direction cosines between the x-, y-, and z-axes and the x' axis, respectively;
$d_{yx}$, $d_{yy}$, and $d_{yz}$ are direction cosines between the x-, y-, and z-axes and the y' axis, respectively;
$d_{zx}$, $d_{zy}$, and $d_{zz}$ are direction cosines between the x-, y-, and z-axes and the z' axis, respectively; and
a and b are two detectors in a detector pair.

6. The device of claim 5 wherein said plurality of multipliers includes eighteen said multipliers, one each being provided to multiply one ordinate of one of said detector pair in said primary coordinate system with one said direction cosine as set forth in equations (1) through (6), and wherein said plurality of adders includes six said adders, one each being provided to sum three said products from said plurality of multipliers and one said translational offset as set forth in equations (1) through (6), whereby said transformed coordinates (x', y', z') for each of said pair of detectors are acquired.

7. A method for on-line correction of patient motion in three-dimensional positron emission tomography wherein a positron emission tomograph device is used to collect coincidence event data, said method comprising the steps of:

a) collecting data relative to a scan;
b) calculating an event correction factor (ECF) for said coincidence event and position data, said step of calculating an event correction factor (ECF) for said coincidence event and position data including the steps of:
   i) multiplying a first inverse efficiency value from a first look-up table and second inverse efficiency value from a second look-up table to attain a first normalization factor, said first inverse efficiency value being representative of a first crystal index, and said second inverse efficiency value being representative of a second crystal index;
   ii) multiplying said first normalization factor with a first geometric correction factor to attain a second normalization correction factor;
   iii) multiplying an inverse live-time value from a third look-up table and an inverse live-time value from a random access memory (RAM) to attain a first dead-time correction factor, said third look-up table inverse live-time value being a conversion of a crystal block and polled block singles rates, said RAM inverse live-time value being representative of said crystal block;
   iv) multiplying said first dead-time correction factor with a second geometric correction factor to attain a second dead-time correction factor; and
   v) multiplying said second normalization correction factor with said second dead-time correction factor to attain said event correction factor;
c) converting said coincidence event and position data into (x,y,z) pair content;
d) transforming said (x,y,z) pair into an (x',y',z') pair;
e) converting said (x',y',z') pair into a bin address; and
f) performing on-line weighted histogramming on said bin address using said ECF, said fifth processing circuitry outputting a normalized projection data set.

8. A method for on-line correction of patient motion in three-dimensional positron emission tomography wherein a positron emission tomograph device is used to collect coincidence event data, said method comprising the steps of:
   a) collecting data relative to a scan;
   b) calculating an event correction factor (ECF) for said coincidence event and position data;
   c) converting said coincidence event and position data into (x,y,z) pair content;
   d) transforming said (x,y,z) pair into an (x',y',z') pair, said step of transforming said (x,y,z) pair into an (x',y',z') pair including the steps of:
      i) multiplying selected groups of said data in a plurality of multipliers to simultaneously acquire a plurality products; and
      ii) summing a selected group of said plurality of products in a plurality of adders to acquire a plurality of sums representative of transformed coordinates from a primary coordinate system to a secondary coordinate system;
   e) converting said (x',y',z') pair into a bin address; and
   f) performing on-line weighted histogramming on said bin address using said ECF, said fifth processing circuitry outputting a normalized projection data set.

9. The method of claim 8 in said steps of i) multiplying selected groups of said data in a plurality of multipliers; and ii) summing a selected group of said plurality of products in a plurality of adders, wherein said plurality of multipliers and said plurality of adders are provided to produce transformed coordinates from said primary coordinate system to said secondary coordinate system for each of a pair of detectors using the equations:

$$x_a' = d_{xx}*x_a + d_{xy}*y_a + d_{xz}*z_a + X; \quad (1)$$

$$y_a' = d_{yx}*x_a + d_{yy}*y_a + d_{yz}*z_a + Y; \quad (2)$$

$$z_a' = d_{zx}*x_a + d_{zy}*y_a + d_{zz}*z_a + Z; \quad (3)$$

$$x_b' = d_{xx}*x_b + d_{xy}*y_b + d_{xz}*z_b + X; \quad (4)$$

$$y_b' = d_{yx}*x_b + d_{yy}*y_b + d_{yz}*z_b + Y; \quad (5) \text{ and}$$

$$z_b' = d_{zx}*x_b + d_{zy}*y_b + d_{zz}*z_b + Z; \quad (6)$$

where:
   X, Y, and Z are translational offsets from a point (x, y, z) in said primary coordinate system to a point (x', y', z') in said secondary coordinate system;
   $d_{xx}$, $d_{xy}$, and $d_{xz}$ are direction cosines between the x-, y-, and z-axes and the x' axis, respectively;
   $d_{yx}$, $d_{yy}$, and $d_{yz}$ are direction cosines between the x-, y-, and z-axes and the y' axis, respectively;
   $d_{zx}$, $d_{zy}$, and $d_{zz}$ are direction cosines between the x-, y-, and z-axes and the z' axis, respectively; and
   a and b are two detectors in a detector pair.

10. The method of claim 9 wherein said plurality of multipliers includes eighteen said multipliers, one each being provided to multiply one ordinate of one of said detector pair in said primary coordinate system with one said direction cosine as set forth in equations (1) through (6), and wherein said plurality of adders includes six said adders, one each being provided to sum three said products from said plurality of multipliers and one said translational offset as set forth in equations (1) through (6), whereby said transformed coordinates (x', y', z') for each of said pair of detectors are acquired.

11. The method of claim 8, before said step of i) multiplying selected groups of said data in said plurality of multipliers, further comprising the step of normalizing said data.

12. The method of claim 11, before said step of i) multiplying selected groups of said data in said plurality of multipliers, and after said step of normalizing said data, further comprising the step of histogramming said data.

13. The method of claim 12 wherein said step of histogramming said data includes the steps of:
   i) reading from a memory a current bin value indexed by a bin address;
   ii) applying said bin value produced by said memory together with a normalization value for said current bin to an adder; and
   iii) writing an output of said adder to said current bin.

* * * * *